US006746872B2

(12) United States Patent
Zheng et al.

(10) Patent No.: US 6,746,872 B2
(45) Date of Patent: Jun. 8, 2004

(54) CONTROL COMPOSITIONS AND METHODS OF USE FOR COAGULATION TESTS

(75) Inventors: Xiang Yang Zheng, Fremont, CA (US); Brian Earp, San Jose, CA (US); Herbert Chow, South San Francisco, CA (US); Christa Hartmann, Oakland, CA (US)

(73) Assignee: LifeScan, Inc., Milpitas, CA (US)

( * ) Notice: Subject to any disclaimer, the term of this patent is extended or adjusted under 35 U.S.C. 154(b) by 37 days.

(21) Appl. No.: 10/055,788

(22) Filed: Jan. 16, 2002

(65) Prior Publication Data
US 2003/0153084 A1 Aug. 14, 2003

(51) Int. Cl.[7] .................... G01N 33/86; G01N 31/00
(52) U.S. Cl. ...................... 436/16; 436/8; 436/69; 436/79; 422/61; 422/73; 600/369; 73/64.41
(58) Field of Search .................. 436/8, 16, 63, 436/69, 79, 164, 165; 422/61, 73, 99, 102, 939; 435/2, 13; 600/368, 369; 73/64.41

(56) References Cited

U.S. PATENT DOCUMENTS

| 3,692,487 | A | | 9/1972 | Sanz | |
|---|---|---|---|---|---|
| 4,097,238 | A | | 6/1978 | Ashley | |
| 4,847,209 | A | * | 7/1989 | Lewis et al. | 436/533 |
| 5,110,727 | A | | 5/1992 | Oberhardt | |
| 5,246,666 | A | * | 9/1993 | Vogler et al. | 422/73 |
| 5,427,913 | A | * | 6/1995 | Shaw et al. | 435/7.21 |
| 5,455,009 | A | * | 10/1995 | Vogler et al. | 422/102 |
| 5,854,005 | A | * | 12/1998 | Coller | 435/7.21 |
| 5,858,648 | A | * | 1/1999 | Steel et al. | 435/5 |
| 5,994,139 | A | * | 11/1999 | Jacobs et al. | 436/10 |

FOREIGN PATENT DOCUMENTS

| EP | 0974840 A2 | 1/2000 |
|---|---|---|
| JP | 09266798 | 10/1997 |
| WO | WO 9603655 | 2/1996 |

OTHER PUBLICATIONS

L. Poller "The Prothrombin" World Health Organization, pp 1–32, 1998.

* cited by examiner

Primary Examiner—Maureen M. Wallenhorst
(74) Attorney, Agent, or Firm—Carol M. LaSalle; Bozicevic, Field & Francis, LLP

(57) ABSTRACT

Compositions, methods, devices and kits for use in the calibration of coagulation tests. The control compositions include particles capable of aggregating in plasma and calcium ions which, when mixed with plasma, simulate the behavior of whole blood in a coagulation test. The methods include providing calcium ions and particles capable of aggregating in plasma, combining the particles and calcium ions with plasma to form a control composition, and applying the control composition to a coagulation test. The devices include a container having at least two compartments, with one compartment including particles that promote or induce aggregation of a protein or proteins in plasma, and the other compartment includes a solution of calcium ions. The kits include a control composition including a container of calcium ions, a container of particles capable of inducing aggregation of proteins in plasma, and one or more coagulation test devices.

42 Claims, 2 Drawing Sheets

CONTROL COMPOSITIONS AND METHODS OF USE FOR COAGULATION TESTS

BACKGROUND OF THE INVENTION

A variety of blood and plasma coagulation tests have been developed for diagnosis of coagulation disorders, monitoring of patient anti-coagulation therapies, screening of patients for coagulation ability prior to surgery, and other uses. Such tests include, for example, the prothrombin time (PT), partial thromboplastin time (PTT), activated partial thromboplastin time (APTT), thrombin clotting time (TCT), activated clotting time (ACT), fibrinogen assays, and other tests.

The prothrombin time or PT test is the most frequently used coagulation test, and is typically employed to monitor patients undergoing oral anticoagulation therapies with drugs such as warfarin or coumadin. The PT evaluates the extrinsic coagulation pathway factors by measuring the ability of a patient's recalcified plasma or capillary blood to clot when mixed with thromboplastin. Accurate monitoring of patients is required to regulate drug dosage and avoid massive bleeding or recurrence of thrombosis. Prothrombin time assays typically involve exposing a patient blood sample to thromboplastin, and then monitoring the time required for gelling or clotting of the blood or plasma. The thromboplastin may be present in a liquid reagent mixable with blood, or may be in the form of a chemical pre-dried on a test strip to which blood is applied, or arranged in other test format. The development of clotting is the—onset of the thromboplastin reaction, and the onset time may be detected optically, electrically, by viscosity change, or other techniques.

Non-uniformity of PT test results can lead to dosage control problems for patients. The variation in PT has long been recognized as a serious problem, and the World Health Organization (WHO) has developed standards for establishment of uniformity of PT tests. The International Sensitivity Index (ISI) is a correction factor for the response of different thromboplastins to oral anticoagulants (L. Poller, "The Prothrombin Time", WHO 1998). The ISI value depends upon a calibration of an individual PT test against a reference preparation such as the WHO International Reference Preparation (IRP). The ISI must be determined for every commercial lot of PT test devices to provide a compensation for non-uniformity of test systems.

Prothrombin times obtained using different coagulation tests can be compared by the calculation called the International Normalized Ratio (INR). The INR provides a compensation for system-to-system variations in the determination of PT, and is calculated by dividing the PT time by the Mean Normal Prothrombin Time (MNPT) of a defined normal subject population and raised to the power of ISI. Different types of PT tests may generate different PT results from the same sample, but the INR values for the different tests should be comparable. The ISI is a part of the INR calculation to correct for the difference in sensitivity of the PT test system. The ISI is derived from the slopes of the calibration lines of the log of reference PT values versus testing PT values obtained from 20 normal (non-anticoagulated) subjects and sixty stabilized patients undergoing long-term orally administered anti-coagulation therapy. The MNPT value is typically obtained by calculating the geometric mean of testing PT from 20 normal subjects used in the ISI determination.

The calibration of coagulation tests in the manner recommended by the WHO is a relatively complex and expensive procedure. Calibration of each commercial lot of PT tests requires capillary blood samples from a group of at least 80 donors with wide range of INR. Since the aging blood samples cannot be used in PT tests, fresh blood samples typically must be obtained from donors for each new commercial lot of PT tests. The acquisition of blood samples in this manner is costly and requires obtaining numerous patient consents for blood drawing for evaluation of each commercial lot of PT tests.

One attempt to overcome the aforementioned difficulties has been use of commercially available "calibration" plasmas that are derived from pools of normal and anti-coagulated blood donors and which can be stored frozen. Five to seven different levels or types of calibration standards are generally required, depending upon the particular test to be calibrated. However, many coagulation tests are based on optical detection of blood coagulation in a test strip, which allows quick and easy PT testing by individual patients using "finger stick" blood samples in non-clinical settings. Such coagulation tests cannot effectively detect coagulation in plasma alone, and the effectiveness of calibration plasmas as control standards for coagulation tests has thus been limited.

There is accordingly a need for calibration and control compositions and methods for coagulation tests that are simple and inexpensive to use, which do not require large blood or plasma donor pools, and which are usable with optical detection systems. The present invention satisfies these needs, as well as others, and generally overcomes the deficiencies found in the background art.

SUMMARY OF THE INVENTION

The invention provides control compositions, methods, devices and kits for use in the calibration of coagulation tests. The subject control compositions comprise, in general terms, particles capable of aggregating in plasma, and calcium ions. The composition may additionally comprise plasma. The plasma may comprise a citrated calibration plasma derived from a pool of known anti-coagulated human blood donors, citrated control plasma derived from diluting or depleting pooled normal plasma, or other plasma. The particles may comprise polymeric beads having a plurality of charged groups on surfaces thereof which undergo non-specific binding to proteins present in the plasma. The calcium ions may be in the form of a solution of $Ca^{++}$ ion such as a calcium halide solution or solution of other soluble calcium salt. The compositions, in certain embodiments, may comprise a solution or suspension of particles capable of aggregation in citrated plasma, a solution of calcium ions that can be combined with the suspension of particles, and citrated plasma that can be mixed with the combined calcium ion solution and particle suspension.

The subject compositions may further comprise one or more optical contrast enhancers to facilitate optical detection of plasma coagulation. The optical contrast enhancers may comprise one or more particulate pigments and/or a soluble dye or dyes. —The optical contrast enhancer(s) may be dissolved and/or suspended in a solution with the calcium ions. The particles or polymeric beads may also include a dye or pigment for contrast enhancement. The subject compositions may further comprise hemoglobin to facilitate particle aggregation in plasma. Various components of the control compositions may be stored separately prior to use to maximize shelf life. The compositions may additionally comprise an antifreeze to facilitate low-temperature storage of the compositions or components thereof.

The subject methods comprise, in general terms, providing calcium ions and particles capable of—aggregation in plasma, combining the calcium ions and particles with plasma to form a control composition, and applying or introducing the control composition to at least one coagulation test. The methods may further comprise monitoring coagulation of the control composition. The methods may additionally comprise determining a relationship between coagulation time of the control composition and the coagulation time of at least one whole blood sample associated with the plasma used in the control composition. The method may further comprise determining a relationship between a coagulation time for the control composition obtained from the coagulation test, and a coagulation time using a reference test. The method may still further comprise determining a calibration curve or assigning a calibration for the coagulation test. In certain embodiments, the method may comprise providing a first control component including calcium ions, providing a second control component including particles capable of aggregation in plasma, combining the first and second control components together, adding plasma to the combined control components to form a control composition, applying or introducing the control composition to at least one coagulation test specimen, and monitoring coagulation of the control composition.

The invention also provides devices or apparatus for storing separate components of the subject control composition. The devices comprise generally a container having at least two compartments, with one compartment including particles that can aggregate in plasma, and the other compartment including a solution of calcium ions. The compartments are configured such that the contents in the two compartments cannot be mixed together prior to carrying out calibration testing. The compartments may be defined by one or more movable or frangible barriers that are removed or broken to allow mixing of the compartment contents prior to use. The particles may comprise a solution of polymer beads having charged groups on surfaces thereof. The calcium ion solution may comprise a calcium chloride solution, and may include optical contrast enhancers such as a dye or dyes and hemoglobin as a bead particle aggregation enhancer. The container may include an additional compartment that contains a plasma that is mixable with the contents of the other two compartments.

The subject kits may comprise a control composition comprising a container of calcium ions, a container of particles capable of aggregation in plasma, and a container of calibration plasma. The kits may further comprise one or more coagulation test devices such as PT test strips. The kits may additionally comprise a reader for measuring coagulation time for the coagulation test device. The kits may also include printed instructions for mixing the control composition with the calibration plasma, applying the control composition and plasma to the coagulation test device, and measuring a coagulation time. The containers of calcium ions, blood plasma and/or particles capable of aggregation in plasma may be embodied in separate compartments in a single container.

BRIEF DESCRIPTIONS OF THE DRAWINGS

The present invention will be more fully understood by reference to the following drawings, which are for illustrative purposes only.

DETAILED DESCRIPTION OF THE INVENTION

Figure 1:
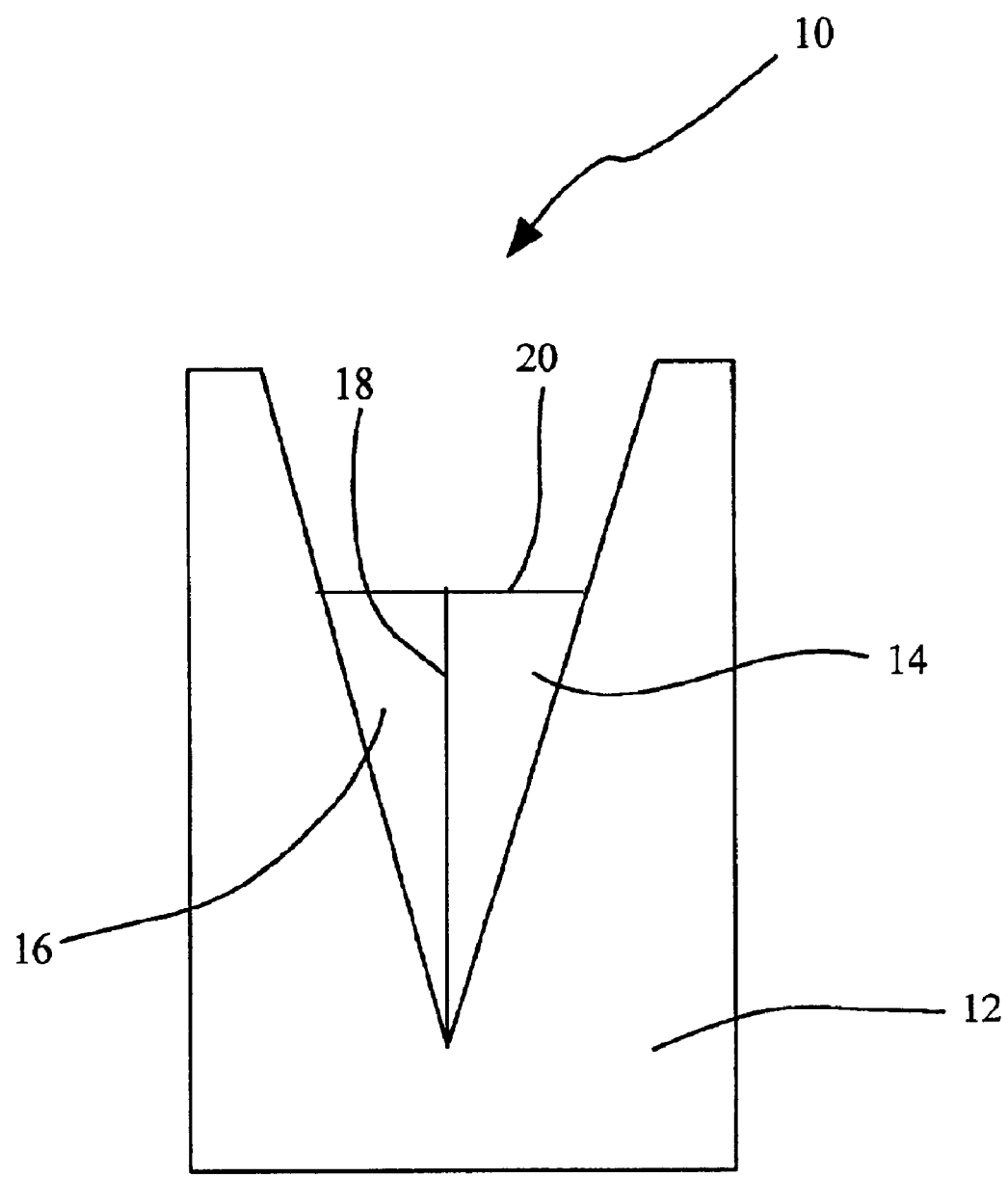
FIG. 1 is a schematic diagram of one embodiment of a control composition device in accordance with the invention.

Before the subject invention is described further, it should be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Disclosed herein are compositions, methods, devices and kits for calibration of coagulation tests. The invention utilizes a suspension of particles capable of aggregation in plasma, and a solution of calcium ions to form a matrix that, when combined with plasma, provide a control composition that mimics the action of whole blood when applied or introduced to a coagulation test system such as a test strip. The combined particles, calcium ion solution and plasma of the control composition, when used in a coagulation test, simulate the coagulation behavior of the corresponding whole blood from which the plasma of the control composition was derived. The control compositions thus provide for quick and easy calibration of coagulation tests, and allow quality control for commercial lots of coagulation tests.

The invention is described primarily in terms of use with PT tests, and optically readable PT test strip systems in particular. The invention may be used, however, for calibration and for quality control with any type of blood or plasma coagulation test, including, by way of example and not of limitation, partial thromboplastin time (PTT) tests, activated partial thromboplastin time (APTT) tests, thrombin clotting time (TCT) tests, activated clotting time (ACT) tests, fibrinogen assays, and other coagulation tests associated with blood and plasma that detect coagulation optically, electrically, viscosimetrically, or other detection mechanism.

The definitions herein are provided for reason of clarity, and should not be considered as limiting. The technical and scientific terms used herein are intended to have the same meaning as commonly understood by one of ordinary skill in the art to which the invention pertains.

The term "average bias" and grammatical equivalents thereof as used herein means a measure of the accuracy of an experiment, test, method or technique. The "average bias" is the difference between the mean result of one data set from an experiment and the means result of another data set from the experiment.

The term "coefficient of variation" or "CV" and grammatical equivalents thereof as used herein means the statistical value that quantifies the precision of a measurement. The term "% CV" is equal to (Standard Deviation/Mean)× 100.

The term "prothrombin time" or "PT" and grammatical equivalents thereof as used herein means tests for blood coagulation time that are usable to monitor treatment of individuals who are at risk of excessive blood clotting (thrombosis). Since the "PT" for a given sample will vary when measured with different PT testing systems, "PT" values are normalized by expressing tests results in terms of International Normalized Ratio (INR) units.

The term "International Normalized Ratio" or "INR" and grammatical equivalents thereof as used herein refers to a unit of measurement derived from prothrombin time PT according to the equation $$INR=(PT/MNPT)^{ISI}$$

wherein MNPT is the Mean Normal Prothrombin Time and ISI is the International Sensitivity Index. The INR compensates for system-to-system variation and the sensitivity of the thromboplastin reagent in the determination of PT. While different reagents and instrument systems are expected to generate different PTs for the same sample, the INR values for the different systems are expected to be comparable. The normal INR range is from between about 0.8 to about 1.2 INR units, and therapeutic levels may vary between about 2.0 and about 4.5 INR units, depending upon the thrombotic risk to a patient and different therapies involved.

The term "International Sensitivity Index" or "ISI" and grammatical equivalents thereof as used herein refers to a factor used to convert PT to INR units. The ISI is unique to each system used for PT testing, and must be determined by calibrating the system against a reference system. The ISI is calculated by multiplying the calibration curve slope (orthogonal regression wherein x=LogPT of the system to be calibrated and y=LogPT of the reference system) by the ISI of a reference system.

The term "Mean Normal Prothrombin Time" or "MNPT" and grammatical equivalents thereof as used herein refers to a factor used to convert PT to a Prothrombin Time Ratio (PTR) or to INR units using the ISI factor. The MNPT is the geometric mean of the clotting times of several (generally more than 20) normal plasmas tested on a PT test system. The MNPT is unique to each coagulation time test system.

The term "calibration code" and grammatical equivalents thereof as used herein means a unique number or set of numbers used in different analytical systems to identify the combination of ISI and MNPT for a given lot of PT test reagents such as test strips.

The term "plasma" and grammatical equivalents thereof as used herein means blood plasma, i.e., the acellular fluid in which blood cells are suspended.

The term "host", "patient", "individual" and "subject" and grammatical equivalents thereof as used herein means a member or members of any mammalian or non-mammalian species that may be a plasma donor for plasmas usable with the invention, or may be in need of anti-coagulation therapy, or otherwise require coagulation monitoring.

The term "coagulation" and grammatical equivalents thereof as used herein means a transformation of a liquid or sol into a soft, semi-solid or solid mass. Blood naturally coagulates to form a barrier when trauma or pathologic conditions cause vessel damage. There are two well-recognized coagulation pathways: the extrinsic or thromboplastin-controlled and the intrinsic or prothrombin/fibrinogen-controlled coagulation pathway.

It should be noted that, as used in this specification and the appended claims, the singular forms "a," "an" and "the" include plural referents unless the content clearly dictates otherwise. Thus, for example, reference to "a control mixture" includes one or more such control mixtures, and "a coagulation test" includes one or coagulation tests, and the like.

Compositions

The control compositions of the invention comprise particles capable of aggregation in plasma and calcium ions that, when combined with plasma, mimic the action of whole blood when applied or introduced to a coagulation test system such as a test strip. Particularly, the aggregation of the particles and proteins, together with the activation of an extrinsic coagulation pathway, act in a manner similar to whole blood that allows calibration of coagulation test systems. The particles may be in the form of a suspension, and calcium ions in a solution, that are stored separately prior to combining with plasma, and may be stored at reduced temperature to prolong storage life. The terms "suspension" and "solution" may be used interchangeably herein, as the subject compositions in many instances will have both dissolved and suspended components present simultaneously.

The particles capable of aggregation in plasma include molecules or functional groups present on the particle surfaces that promote non-specific binding of proteins in plasma to the particles or specific functionalized groups attached on the particle surfaces that lead to detectable particle aggregation for calibration and control of coagulation test systems. The particle size may vary, for example, from about 0.01 micron (uM) to about 1000 uM in diameter. More typically, the particles may have diameters in the range of from about 0.05 uM to about 100 uM and, in some instances, will have diameters ranging from about 0.1 uM to about 10 uM. The particles may comprise a mixture of particles of different sizes in some instances.

The particles may be stored separately from the calcium ion solution, with the particles stored in the form of a suspension in water, aqueous buffer or other liquid, prior to use in calibration as described below. Where the particles are stored as a suspension, the particles may comprise between about 1% weight and about 99% weight of the suspension. In certain embodiments, the weight percent of particles in suspension may comprise between about 10% weight and about 50% weight percent of the suspension. The use of particles in suspended form allows accurate sampling of the suspension with a micropipette.

The compositions of the invention may comprise an antifreeze ingredient in which the particles are suspended, to prevent modification of the particles during cold storage. The antifreeze material may comprise glycerol, ethylene glycol, propylene glycol, or solutions, mixtures or admixtures thereof. In selected embodiments, the aforementioned particles may be suspended directly in an antifreeze ingredient such as glycerol.

The particles may comprise polymeric beads such as polystyrene, polycarbonate, polyacrylic or other polymeric material that has been surface modified to introduce functional groups on the bead surfaces. A variety of such surface functionalized polymeric beads of different polymeric materials, bead sizes, and functionalities are commercially available. The size of the surface-functionalized polymeric beads may vary depending upon the particular embodiment of the invention. The polymer beads may, for example, have a diameter in the range of from about 0.01 uM to about 1000 uM, or in the range of from about 0.05 uM to about 100 uM and, in some instances, in the range of from about 0.1 uM to about 10 uM as noted above.

The functional groups present on the surfaces of the polymer beads induce or promote non-specific aggregation of the beads when the beads are exposed to plasma proteins. The functional groups may comprise charged functional groups, which may include any anionic and/or cationic charged functional group. Anionic functional groups include, by way of example, carboxylate groups, sulfonate groups, phenolate groups and phosphate groups. Cationic functional groups include, by way of example, ammonium, alkylammonium and arylammonium groups. The anionic or cationic functional groups may be introduced onto the polymer beads by surface functionalization chemical reactions. The techniques involved in the introduction of charged functional groups onto polymer bead surfaces may be the same as, or similar to, the well known techniques used in preparation of anionic and cationic beads for ion exchange chromatographies, and a variety of surface-functionalized polymeric beads usable in the subject compositions are commercially available. In the specific examples discussed below, carboxylate-functionalized polystyrene beads are used in a control composition.

The relative concentration of functional groups on particle surfaces may vary. In the case of charged functional groups, the particles may have a surface titration, in microequivalents per gram, of between about 10 and about 1000, more typically between about 50 and about 500 and, in certain embodiments between about 100 and 250. The "parking area" for charged groups on particle surfaces may, for example, be within the range of from about 5 to about 100, from about 10 to about 50 and, in certain embodiments, from about 20 to about 30.

The polymeric material of the beads may be ionomeric in nature such that the charged functional groups are intrinsic to the polymeric material of the beads themselves. Examples of ionomeric polymers include polylysine which provides ammonium functional groups, and polyacrylic acid which provides carboxylate functional groups. The polymeric beads thus may comprise cross-linked ionomer.

The particles may in some instances comprise non-polymeric particles that have undergone surface modification to introduce functional groups. Thus, suitably functionalized particles of carbon, silica, clay or other material may be used in the subject compositions. Charged functional groups may be introduced to such non-polymeric particles by surface functionalization chemistry techniques known in the art, or by coating the particles with an ionomeric polymer such as polylysine or polyacrylic acid.

The subject particles, in some embodiments, may be coated with a material or molecules that promote particle aggregation in plasma. In this regard, the particles may comprise proteins immobilized on the particle surfaces that induce particle aggregation in the presence of plasma.

The calcium ion solution may comprise any water or aqueous-soluble $Ca^{++}$ salt, including, for example, calcium sulfate, calcium halides such as calcium chloride, calcium bromide or calcium iodide. The concentration of the $Ca^{++}$ ion in the solution may vary depending upon particular embodiments of the invention and the solubility of the particular calcium salt used. The concentration of $Ca^{++}$ ion may be, for example, in the range of from about 0.01 Molar to 5.0 Molar, and more typically in the range of from about 0.05 Molar to about 2.0 Molar. In specific embodiments, the concentration of $Ca^{++}$ ion may be in the range of from about 0.1 Molar to about 1.0 Molar. The calcium ion solution is generally stored separately from the particles, and is mixed therewith prior to carrying out the methods of the invention as described further below.

Control compositions comprising polymeric beads having charged functional groups on the bead surfaces, together with a solution of a soluble calcium salt, when mixed with citrated plasma, provide an effective mimic of the coagulation of regular whole blood that can be used for calibration of coagulation tests as described further below. Some coagulation tests cannot easily detect coagulation in an un-pigmented control composition. Thus, in embodiments of the invention that are used to calibrate coagulation tests based on optical monitoring of coagulation, one or more optical contrast enhancers may be included to aid in the optical monitoring of coagulation.

The optical contrast enhancer may comprise suspendable or soluble colored material or pigment, and may be suspended or dissolved in the solution of calcium ion, suspended or dissolved in a solution with the polymeric beads or other particles, or suspended or dissolved in a separate liquid. The optical contrast enhancer may additionally, or alternatively, comprise a soluble dye present in the calcium ion solution, and/or a dye present in the polymeric beads, or dissolved in a solution in which the beads are suspended. The color of the dye(s) may be varied depending upon the wavelength used to characterize coagulation in the coagulation test to be calibrated. In the case of conventional red LED light sources, blue dyes capable of absorbing the red LED output can be used. The amount of dye used may vary depending upon particular embodiments of the invention and intensities of individual dyes. Where a dye is dissolved in the calcium ion solution, the dye may comprise, for example, between about 0.01 percent weight and about 10 percent weight of the solution. In certain embodiments, the dye may comprise between about 0.1 percent weight and about one percent weight, and in specific embodiments may comprise between about 0.1 percent weight and 0.5 percent weight.

The composition may further comprise a particle aggregation enhancer that is independent of the particles themselves, i.e., that is not associated with the particle surfaces. Hemoglobin is a desirable aggregation enhancer in many embodiments because hemoglobin tends to facilitate the aggregation of beads and other particles in plasma. Particularly, crude preparation of hemoglobin provides lipid membrane that aids particle aggregation, and provides cell surface charges that are similar to blood cells and thus facilitate aggregation. The polymeric beads or other particles, together with hemoglobin, mimic the "Rouleau effect" such that optical readout of the control composition will show an increase in percent transmittance as the beads aggregate, with the percent transmission leveling off as coagulation occurs.

Many hemoglobins are commercially available as dry or lyophilized erythrocytes and may be used with the invention. Where hemoglobin is used as an aggregation enhancer in the calcium ion solution, the hemoglobin may comprise, for example, between about one percent weight and about twenty five percent weight of the solution and, in certain embodiments, from between about five percent weight and about 15 percent weight.

The control compositions of the invention may also comprise various other components or ingredients to facilitate or promote particle aggregation in plasma. Dissolved and/or suspended polyvinylpyrrolidone (PVP) and polyethylene glycol (PEG) are examples of aggregation enhancers that may be used with the invention. In cases where the subject compositions are used to calibrate coagulation tests wherein coagulation time is determined electrically, according to potential measured across a sample between electrodes, one or more electrolyte modifiers may be included in the compositions to facilitate voltage measurement. Such electrolyte modifiers may include, for example, solutions of sodium or potassium salts or other soluble electrolytes.

The control compositions may also include plasma, which may be in the form of a human "calibration plasma" that has been obtained from pools of coagulation-normal blood donors or donors of known coagulation ability. The plasma may be citrated to prevent clotting. The citrate is typically present in the form of a soluble citrate salt that is provided in blood and plasma collection tubes, and which is transferred to the plasma from the collection tubes. The citrate serves to chelate calcium ions in the plasma to prevent clotting. Where the inventive compositions are used in association with coagulation tests for non-human subjects, plasma may be obtained from members of the corresponding subject species.

The subject control compositions may, in certain embodiments, also comprise one or more clotting factors such as thromboplastin, fibrinogen, FVII, FVIIa and the like, that are usable to activate an extrinsic coagulation mechanism in plasma. However, it is generally contemplated that the coagulation tests with which the subject compositions are used will include a clotting factor so that clotting factors are not required in the compositions.

General Methodologies

The subject methods comprise providing a composition including calcium ions and particles capable of aggregation in plasma, combining the composition with plasma, and introducing the combined particles, calcium ion solution and plasma to a coagulation test to be calibrated. More specifically, the subject methods may comprise providing particles capable of aggregation in plasma, providing a solution of calcium ions, combining the particles and solution of calcium ions, adding plasma to the combined particles and solution of calcium ions to form a control composition, introducing or applying the control composition to a coagulation test, and monitoring coagulation of the control composition. The methods may further comprise determining a relationship between coagulation time of the control composition and the coagulation time of whole blood from which the plasma in the control composition was derived. The methods may additionally comprise determining a relationship between a coagulation time for the control composition obtained from the coagulation test and a coagulation time for a reference test. The methods may still further comprise determining a calibration curve or calibration assignment for the coagulation test. The methods may yet further comprise applying the control composition to a plurality of coagulation tests, monitoring coagulation of the control compositions for each of the coagulation tests, and evaluating quality control for each of the coagulation tests.

The providing of particles capable of aggregation in plasma may comprise providing a suspension of particles. The particles may comprise polymeric beads having charged or other specific functional groups on surfaces thereof. The particles may be suspended in an antifreeze such as glycerol, or in other liquid, as related above. The particles may be pigmented or otherwise contain a dye to facilitate optical detection of plasma coagulation. The suspension of particles in antifreeze may be stored frozen. The amount of polymeric beads or other particle provided will generally vary depending upon the type of calibration test to be calibrated. The amount or volume of particle suspension provided may comprise, for example, a volume of between about five $\mu L$ and about 500 $\mu L$, between about 10 $\mu L$ and 100 $\mu L$, or between about 25 $\mu L$ and 50 $\mu L$ of bead suspension. The bead suspension thus provided may be stored in a freezer prior to use.

Providing a calcium ion solution may comprise providing a solution of any water or aqueous-soluble $Ca^{++}$ salt, including calcium sulfate, or calcium halides such as calcium chloride, calcium bromide or calcium iodide, or the like as described above. Providing the calcium ion solution may further comprise providing one or more optical contrast enhancers and/or particle aggregation enhancers in the solution, such as dissolved dye and/or hemoglobin as described above. The amount of calcium ion solution provided will generally vary depending upon the type of calibration test to be calibrated. The amount of calcium ion solution provided may comprise, for example, a volume of between about five $\mu L$ and about 500 $\mu L$, between about 10 $\mu L$ and 100 $\mu L$, or between about 20 $\mu L$ and 40 $\mu L$ of 1.0 Molar stock solution. The calcium ion solution thus provided may be stored in a freezer prior to use.

The particles and calcium ion solution, if freezer-stored, should be brought up to ambient temperature prior to mixing thereof. The temperature adjustment should be effected shortly prior to adding or mixing plasma with the separate stored particles and calcium ion solution as described below. The combining or mixing may be carried out by pipetting suitable quantities of particle suspension and calcium ion solution to a common container, and then vortexing, rocking or otherwise agitating the container to effect mixing. The storage of the particles and calcium ion solution and subsequent mixing thereof may also be carried out using a dual compartment container device as described further below.

Next, plasma is added to the combined particles and calcium ion solution to form a control composition. The plasma may comprise citrated calibration plasma derived from a pool or pools of blood donors, such as 20 normal persons and 60 anti-coagulation patients according to WHO procedure. The plasma may also comprise a citrated human calibration or control plasma such as those commercially obtainable from Precision Biologics Inc., Dade Behring, Instrumentation Laboratory, Pacific Hemostasis, Inc., Haematologic Technologies, Inc., Bio Rad, Inc., or other commercial source. The amount of plasma added to the combined particles and calcium ion may comprise, for example, a volume of from about 5 $\mu L$ to about 500 $\mu L$, or, in certain embodiments, a volume of between about 10 $\mu L$ and about 250 $\mu L$, or, in some embodiments, a volume of between about 50 $\mu L$ and about 200 $\mu L$. The plasma may be brought up to room or ambient temperature prior to addition to the combined particles and calcium ion solution.

The time duration between the mixing of the particles and calcium ion solution and the subsequent adding of plasma thereto to may comprise from between about 10 seconds to about one hour, and in certain embodiments may comprise a duration of from between about 30 seconds to about 30 minutes, or from between about one minute to about 10 minutes.

After addition of the plasma the particles and calcium ion solution to form a control composition, the control composition is introduced to or otherwise applied to a coagulation test to be calibrated. The coagulation test includes a coagulation or clotting factor such as thromboplastin, fibrinogen, FVII, FVIIa or the like, that can activate an extrinsic coagulation mechanism in the plasma present in the control composition, to which the control composition is exposed. The coagulation test may comprise a prothrombin time (PT) test, a partial thromboplastin time (PTT) test, an activated partial thromboplastin time (APTT) test, a thrombin clotting time (TCT) test, an activated clotting time (ACT) test, a fibrinogen assay, or other coagulation test associated with blood and/or plasma as noted above. The coagulation test may be configured to detect coagulation optically, electrically, viscosimetrically, or by other technique. Exemplary coagulation tests systems with which the subject compositions and methods may be used include those described in U.S. Pat. Nos. 3,620,676, 3,640,267, 4,088,448, 4,426,451, 4,849,340, 4,868,129, 5,110,727, 5,230,566, 5,472,603, 5,522,255, 5,526,111, 5,700,695, 5,710,622, 5,736,404, 5,789,664, 6,084,660, 6,046,051, 6,060,323 and 6,066,504, and European Patent Applications EP 0 803 288 and EP 0 974,840, the disclosures of which are incorporated herein by reference.

Introduction of the control composition to the coagulation test may be carried out in generally the same manner used to introduce a whole blood sample or a plasma sample to the coagulation test. In the case of an optically readable coagulation test strip, for example, a sample of the control composition may be taken up into the test strip via suction or capillary action to a location wherein the control composition is exposed to a clotting factor, and wherein one or more sensors are positioned to optically detect coagulation of the control composition in the test strip. Optical detection may be achieved by measurement of optical reflectance, absorption, transmission or other effect associated with the test strip in a conventional manner.

The control composition is introduced to the coagulation test relatively shortly after addition of the plasma to the particles and calcium ion solutions, as the calcium ion solution and charged functional groups on the particles are effective to induce bead aggregation in the plasma upon contact of the plasma with the particles and calcium ion solution. Thus, the control composition may be introduced to the coagulation test between about one second and about 20 minutes after addition of the plasma to the combined particles and calcium ion solution, or, in certain embodiments, after a duration of between about five seconds and about ten minutes.

Following introduction of the control composition to the coagulation test, monitoring coagulation of the citrated plasma is carried out. This monitoring may be achieved via optical, electrical, viscosimetric, or other technique. As noted above, aggregation of particles and optical contrast enhancers within the composition is optically detectable. In certain embodiments the particles, together with crude hemoglobin as an aggregation enhancer, mimic the "Rouleau effect" such that aggregation of the particles and hemoglobin is optically detectable.

From the monitoring of coagulation, the coagulation test can be calibrated and the quality or properties of coagulation tests can be verified or controlled. The coagulation times measured by different coagulation tests will vary due to different test configurations, and different commercial lots of the same coagulation test may vary due to different samples of coagulation factor used in the coagulation test. The variability of different thromboplastin samples used in the same type of PT tests, for example, can result in prescription of incorrect anticoagulant dosage where PT tests have not been properly calibrated.

The WHO international system of PT test standardization utilizes the International Normalized Ratio (INR) and the International Sensitivity Factor (ISI) for calibration of PT tests. The ISI value involves the calibration of a particular "local" thromboplastin extract against a reference thromboplastin preparation such as the WHO international reference preparation (IRP) or a commercial standard with known properties such as RECOMBIPLASTIN®. Methods for determination of ISI values and calibration of PT tests are well known in the art and are described by L. Poller in "The Prothrombin Time", WHO 1998, the disclosure of which is incorporated herein by reference. Briefly, the slope of the orthogonal regression line obtained when PT measurements with local thromboplastin from a donor pool (typically 20 normal and 60 anticoagulant-treated patients) are plotted on a double logarithmic scale against the PT obtained with a thromboplastin standard, to provide a measure of the responsiveness of a PT test. The orthogonal regression calibration slope parameter $b_1$ of the local thromboplastin versus the reference thromboplastin with which it is calibrated is used to calculate an ISI according to the relation $$ISI_{Local} = (b_1 \times ISI_{Reference})$$

The orthogonal regression line parameter $b_1$ is derived from the relationship $y = a_1 + b_1 x$, where $a_1$ and $b_1$ respectively are the intercept and slope of the orthogonal regression line. The value $a_1$ can be shown as $$a_1 = \bar{y} - b_1 \bar{x}$$

wherein $\bar{x}$ and $\bar{y}$ are the arithmetic mean of x and y. The value of $b_1$ can be shown as $$b_1 = m + \sqrt{\sqrt{n^2 - 1}}$$

wherein n is the number of PTs, $$m = \frac{\sum (x - \bar{x})^2 - \sum (y - \bar{y})^2}{2 \sum (x - \bar{x})(y - \bar{y})} = \frac{1}{2r}\left[\frac{s_y}{s_x} - \frac{s_x}{s_y}\right]$$

$s_x$ and $s_y$ are standard deviations of the x and y values, and r is a correlation coefficient.

To account for the variation present in individual PT tests, PT values are normalized by expressing tests results in terms of International Normalized Ratio (INR) units. The INR is a unit of measurement derived from prothrombin time PT according to the equation $$INR = (PT/MNPT)^{ISI}$$

wherein MNPT is the Mean Normal Prothrombin Time and ISI is the International Sensitivity Index as noted above. The Mean Normal Prothrombin Time or MNPT is a factor used to convert PT to INR units using the ISI factor. The MNPT is the geometric mean of the clotting times of several (generally more than 20) normal plasmas tested on a PT test system. The MNPT is unique to each PT test system.

The particles and calcium ion solution of the subject composition are combined with stored plasma from donors to simulate the donor whole blood in a PT test. Donor plasma samples and commercial calibration plasmas can be stored frozen for extended periods of time, and the control compositions of the invention, when prepared with such plasmas, thus eliminate the expense and inconvenience of obtaining multiple whole blood samples each time a different commercial lot of PT tests must be calibrated. Instead, frozen plasma samples are thawed and mixed with the particles and calcium ion solution to provide a control composition that simulates whole blood each time a test calibration is needed.

While the control compositions of the invention mimic the action of whole blood in PT tests, the PT generated by the control compositions may differ from the corresponding whole blood that supplied the plasma for the compositions. The methods of the invention thus may comprise determining the relationship between a control composition and whole blood that corresponds to or is associated with the plasma used in the control composition. This determination may comprise determining the ISI for the composition, which can be obtained from the slope of the orthogonal regression line of PT measurements of the control composition plotted on a double logarithmic scale against the PT measurements from the corresponding whole blood from which the plasma in the compositions was derived. Where the slope of the orthogonal regression line is $a_1$, the relationship $$ISI_{WB} = (1/a_1) \times ISI_C)$$

is used, wherein $ISI_C$ is the ISI of the control composition, and $ISI_{WB}$ is the ISI of the whole blood corresponding to the plasma in the control composition. As shown in the following specific examples, the $a_1$ for one embodiment composition is approximately 0.81.

Once the relationship between the control compositions and corresponding whole blood has been determined, a determination can be made of the relationship between PT for a control composition obtained from a PT test of interest, and the PT for the control composition obtained from a reference test. The WHO procedure for testing "inter-batch" lots of manufacturers' PT tests recommends a full calibration using orthogonal regression analysis from PTs of whole blood samples versus PTs from corresponding fresh plasma. WHO procedures also permit calibration using certified calibration plasmas.

PT tests that are designed for easy home use by patients are typically based on test strips to which fresh whole blood from a finger stick is applied, with PT monitored optically by a reader. Accurate measurement of PTs using plasma alone for "inter-batch" calibration of such tests is difficult because of the lack of optically detectable red blood cells in plasmas. The control compositions of the invention, however, mimic the behavior of whole blood in optically read PT tests due to optically detectable aggregation of the surface-charged particles in the control compositions. The optical contrast provided by the control compositions during coagulation can be modified or tailored to desired properties by the presence of optical contrast enhancers such as pigment present in the particles themselves, the presence of crude hemoglobin lysate, or other optically detectable particulate pigment as noted above.

The determination of the relationship between PT for a control composition obtained from a PT test of interest, and the PT for a reference test, may be obtained from the orthogonal regression line of PT measurements of the control compositions as measured by the test of interest plotted on a double logarithmic scale against the PT measurements determined from the reference test with a reference thromboplastin. The reference test may comprise, for example, the MLA Electra 1400C Coagulation Analyzer or other reference test system. The reference thromboplastin may comprise RECOMBIPLASTIN®.

The slope of the orthogonal regression line of PT measurements of the control compositions measured on test of interest versus the PT measurements determined from the reference system provides a calibration line or curve from which a calibration code may be determined and assigned to the test of interest. The calibration code requires both an ISI and an MNPT value. The $ISI_C$ is determined from the slope of the calibration line as described above, and the MNPT value can be determined from the 20 normal individuals of the WHO procedure as the geometric mean of the PT times tested on the PT test system of interest.

Devices

The invention also provides devices usable for calibration of coagulation test systems. Referring to FIG. 1, there is shown a coagulation test calibration and control device 10 comprising a container 12 with at least two compartments 14, 16. Container 12 may be configured in the manner of a conventional Eppendorf tube or otherwise have a configuration that is convenient for vortexing, pipette transfer of reagents or ingredients to and from the container, and/or use of the container in a multi-well format or system in a manner common for biological sample containers. Barrier 18 may be removable rather than frangible. An additional frangible or removable barrier 20 may be included with container 12 as a cover for compartments 14, 16.

Particles capable of aggregation in plasma are stored in one of compartments 14, 16, while a calcium ion solution is stored in the other compartment. The particles may comprise surface functionalized polymeric beads, and may be in a suspension as noted above. The calcium ion solution may include hemoglobin, a dissolved dye and/or other optical contrast or aggregation enhancers as also noted above. The container 12 with particles and calcium ion solution therein may be stored in a freezer prior to use. A suitable amount of plasma is then pipetted into the particles and calcium ion solution in the container 12 and mixed therewith. The combined particles, calcium ion solution and plasma may then be introduced into a coagulation test system in the manner described above. Where barriers 18, 20 are frangible, they may be broken with a disposable pipette tip or other instrument such that the contents of compartments 14, 16 can be combined or mixed together in container 12.

In some embodiments, the container 12 may include three compartments separated by removable or frangible barriers, with the third compartment configured to contain plasma. In use, the barriers are broken or removed to combine the particles, calcium ion solution, and plasma. Container 12 may be configured in a variety of ways. In some embodiments, container 12 may include frangible hollow beads wherein are stored the particles and calcium ion solution of the calibration composition.

Figure 2:
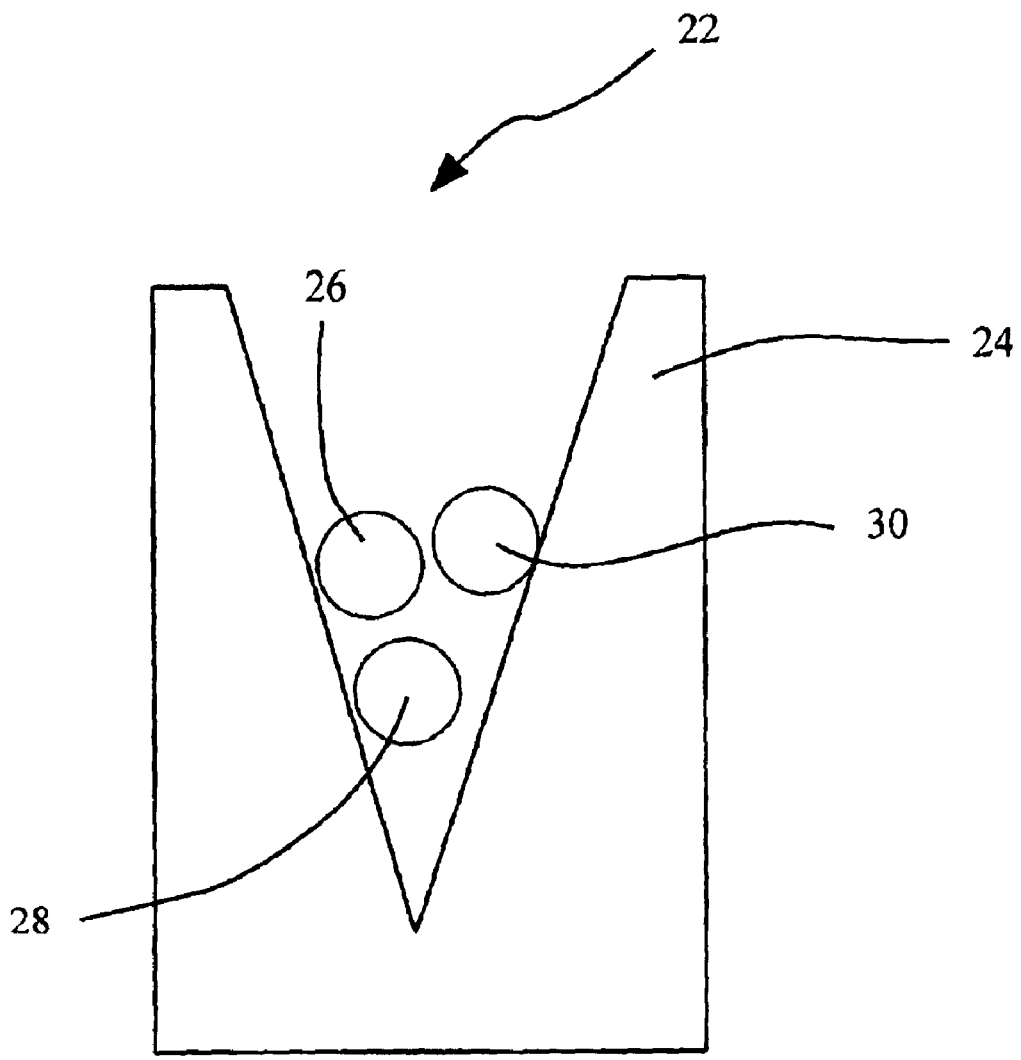
FIG. 2 is a schematic diagram of an alternative embodiment control composition device in accordance with the invention.

Referring to FIG. 2, there is shown an alternative embodiment coagulation test calibration and control device 22 that comprises a container 24 and a plurality of hollow, frangible beads or ampoules 26, 28, 30. Particles capable of aggregation in plasma, a calcium ion solution, and plasma are separately stored within ampoules 26, 28, 30. Breaking the frangible beads allows mixing of the particles, calcium ion solution and plasma to provide a control composition. Container 24 and beads 26, 28, 30 may be stored frozen prior to use as described above.

Kits

Also provided are kits for use in practicing the subject methods. The kits of the subject invention comprise a container of particles capable of aggregation in plasma, and a container of calcium ion. The containers may be in the form of different compartments or frangible beads within a single container as described above. The kits may further comprise one or more containers of a calibration plasma. The kits may additionally, or alternatively, include one or more coagulation test devices such as PT test strips. The kits may include a device or devices for obtaining blood samples, such as a lance for sticking a finger, a lance actuator, and the like. In certain embodiments, the kits also include an automated instrument such as an optical reader for monitoring coagulation in the coagulation test following introduction of the calibration composition to the coagulation test. The kits may additionally include instructions for carrying out the methods for calibrating coagulation tests as described above. These instructions may be present on packaging, a label insert, containers present in the kits, and the like.

Utility

The calibration compositions, methods, devices and kits of the invention may be used for calibration of a variety of coagulation tests used to monitor patients undergoing anticoagulation therapies, or for screening or diagnosis of various conditions in patients or subjects. Such conditions include, by way of example, acquired platelet function defect, congenital platelet function defects, congenital protein C or S deficiency, deep intracerebral hemorrhage; DIC (Disseminated intravascular coagulation), factor II deficiency, factor V deficiency, factor VII deficiency, factor X deficiency, hemolytic-uremic syndrome (HUS), hemophilia A, hemophilia B, hemorrhagic stroke, hepatic encephalopathy, hepatorenal syndrome, hypertensive intracerebral hemorrhage, idiopathic thrombocytopenic purpura (ITP); intracerebral hemorrhage, lobar intracerebral hemorrhage, placenta abruption; transient ischemic attack (TIA), Wilson's disease, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used but some experimental errors and deviations should be accounted for. Unless indicated otherwise, parts are parts by weight, molecular weight is weight average molecular weight, temperature is in degrees Centigrade, and pressure is at or near atmospheric.

Example 1

Preparation of Control Compositions

All reagents and ingredients were used as received from commercial sources unless otherwise indicated. A Cavro dispenser Model RSP 9652 was used for micropipetting.

a. Particle Suspension

Glycerol (0.947 grams, Aldrich/Sigma Cat. No. G7893) was transferred to a 30 mL vial, and 25.71 grams of Bangs carboxy-functionalized polystyrene beads (Bangs Cat. No. DC02B, dark blue P, S/V —COOH, 0.19 $\mu$M average diameter) were added to the glycerol in the vial. The combined glycerol and Bangs beads were vortexed in the vial to form a dark blue bead suspension, and the suspension was stored at room temperature.

b. Pigmented Calcium Chloride Solution

Hemoglobin (3.3 grams, Aldrich/Sigma Cat No. H-3760, dried cow erythrocytes) was transferred to a 50 mL bottle, and 30.0 mL distilled water was added thereto to provide a hemoglobin stock solution. The combined hemoglobin and water was mixed by rocking for 10 minutes to thoroughly dissolve or disperse the hemoglobin. After mixing the bottle of hemoglobin stock solution was placed on ice.

FD&C blue dye powder (0.500 grams, Warner Jenkinson Cat. No. 05601) was added to a separate 15 mL bottle, together with 10.0 mL of distilled water to form a dye stock solution. The bottle was capped and rocked for 10 minutes to dissolve the dye in the water, and the bottle was then stored at room temperature.

In a separate 15 mL bottle, 7.650 mL of 1.0 M $CaCl_2$ solution (BDH Cat. No. 190464K) was mixed with 2.350 mL of distilled water to provide a $CaCl_2$ stock solution. This calcium chloride solution was then stored at room temperature.

Bubbles were removed from the hemoglobin stock solution via pipette, and 27.34 mL of the hemoglobin stock solution was transferred to a 60 mL bottle, followed by addition of 3.66 mL of the $CaCl_2$ stock solution. The combined solutions were mixed, and 2.00 mL of the FD&C dye stock solution was added to the bottle and mixed therein. This pigmented calcium chloride solution was then stored on ice.

c. Combining Particle Suspension and Pigmented Calcium Chloride Solution with Plasmas Into each of several Eppendorf tubes was transferred 37.0 $\mu$L of the particle suspension and 25.0 $\mu$L of the pigmented calcium chloride solution, and the tubes were brought to room temperature prior to the addition of plasma. To each tube was then added 200 $\mu$L of a corresponding plasma sample (see following Examples), and the combined particle suspension, calcium chloride solution and plasma were vortexed for about 3~10 seconds. The combined particle suspension, calcium chloride solution and plasma were applied to the tests strips (described in Example 2 below) within about 30 seconds of mixing.

Example 2

ISI Assignment for Control Compositions

In this Example the determination of the relationship between the control compositions and corresponding whole blood samples from plasmas isolated for the control compositions is demonstrated. The PT test strips and optical reader or meter used in this Example are described in European Patent Application EP 0 974,840, which is incorporated herein by reference as noted above. Briefly, individual strips were made by first passing a double sided adhesive tape (Scapa Tapes. Cat. No. RX 675SLT, Windsor CT) sandwiched between two release liners into a laminating and rotary die-cutting converting system. The pattern shown in FIG. 10 of European Patent Application EP 0 974,840, with the exception of the stop junction, was cut through the top release liner and tape, but not through the bottom release liner. Hydrophilic-treated polyester film (3M Cat. No. 3M9962, St. Paul, Minn.) was laminated to the exposed bottom side of the tape. Thromboplastin (Ortho Clinical Diagnostics, Raritan N.J.) was printed onto the reagent area of the polyester film via bubble jet printer using an HP 51612A print head (Hewlett-Packard, Corvallis Oreg.). A sample port was cut in an untreated polyester film (Adhesive Research Cat. No. AR1235, Glen Rock Pa.), which was then laminated in register to the top of the double sided tape (after removal of the release layer therefrom) to form a three-layer sandwich structure. The stop junction was then die-cut cut trough all three layers of the sandwich, and a strip of single-sided adhesive tape 3M Cat. No. MSX4841, St. Paul Minn.) was applied to the outside of the polyester layer to seal the stop junction. Test strips of this type are commercially available from Lifescan Inc., Milpitas Calif. as HARMONY™ test strips, as well as the corresponding optical reader for the strips.

Clinical site non-venous blood samples and corresponding fresh, citrated plasma samples for 20 normal and 60 anticoagulant treated patients were obtained according to WHO procedure (L. Poller, "The Prothrombin Time", WHO 1998). Frozen tubes containing polymer bead suspension and calcium chloride solution prepared as described above in Example 1 were allowed to warm to ambient temperature, and 200 $\mu$L of each plasma sample was pipetted into a corresponding tube and vortexed for 30 seconds to prepare 20~25 $\mu$L control composition corresponding to each plasma sample. The combined plasma, beads and calcium chloride solution for each sample was applied to the test strips within 30 seconds after vortexing, and a PT time was determined for each sample on a test strip. The corresponding whole blood samples were applied to test strips and PTs were determined therefore. This procedure was repeated at 13 different sample sites for 11 different lots of test strips.

For each lot of strips, the logarithmic values of the PTs obtained from the whole blood samples were plotted against the logarithmic values of the PTs obtained from the control composition samples, and orthogonal regression analysis was used to determine ISI values for the control compositions according to the equation $$ISI_{WB} = (1/a_1) \times ISI_C$$

wherein $ISI_C$ is the ISI of the control composition, and $ISI_{WB}$ is the ISI of the whole blood corresponding to the plasma in the control composition. The values for $ISI_{WB}$ and $ISI_C$ are shown below in Table 1. The average $a_1$ for the control compositions was about 0.8097, and was used in the following Examples as a correction factor for the $ISI_C$.

Example 3

ISI Assignment for PT Test Strips Using Control Compositions with 20/60 Citrate Plasma Samples This example demonstrates the determination of the relationship between the PT values for the control compositions and a reference thromboplastin for calibration of PT test strips. A Hemoliance MLA Electra 1400C Coagulation analyzer was used with Ortho RECOMBIPLASTIN® as a reference. The three channel test strips described in Example 2 were used with the control compositions.

Clinical site citrated plasma samples from the 20 normal and 60 anticoagulant treated patients of Example 2 were stored at −80° C. prior to use. The plasma samples, and frozen tubes containing polymer bead suspension and calcium chloride solution prepared as described above in Example 1, were allowed to warm to ambient temperature. 200 μL of each plasma sample was pipetted into a corresponding tube and vortexed for 3~10 seconds to prepare 262 μL control composition corresponding to each plasma sample. The combined plasma, beads and calcium chloride solution for each sample was applied to a test strip within 30_seconds after vortexing, and a PT time was determined for each sample on a test strip.

The PT for 80 samples of Ortho RECOMBIPLASTIN® standard was measured using the Hemoliance MLA Electra 1400C Coagulation analyzer. The logarithmic values of the PTs obtained from the RECOMBIPLASTIN® were plotted against the logarithmic values of the PTs obtained from the control composition samples made from these 80 samples to provide a calibration line with slope $ISI_C$. The logarithmic values of the PTs obtained from the RECOMBIPLASTIN® were also plotted against the logarithmic values of the PTs obtained from the capillary blood samples to provide a line with slope $ISI_{WB}$. The logarithmic values of the PTs obtained from the control composition samples were also plotted against the logarithmic values of the PTs obtained from the capillary blood samples to provide a line with slope a1. This procedure was repeated for each of the same 11 lots of test strips used in Example 2. The consistency of the slope $a_1$ for each test strip lot is shown in Table 1, together with the $ISI_{WB}$, $ISI_C$, $ISI_C/a_1$, and percent difference between $ISI_{WB}$ and $ISI_C/a_1$ for each lot of test strips. As can be seen from Table 1, the control composition provides a very good approximation of the corresponding whole blood samples for evaluation of the test strips.

TABLE 1

| Strip No. | $ISI_{WB}$ | $ISI_C$ | $ISI_C/0.8097$ | ISI % Difference | $a_1$ |
|---|---|---|---|---|---|
| 1 | 1.17 | 0.96 | 1.19 | 1.3% | 0.8246 |
| 2 | 1.17 | 0.95 | 1.17 | 0.3% | 0.8243 |
| 3 | 1.09 | 0.9 | 1.11 | 2.0% | 0.8482 |
| 4 | 1.19 | 0.97 | 1.20 | 0.7% | 0.8239 |
| 5 | 1.11 | 0.89 | 1.10 | −1.0% | 0.7975 |
| 6 | 1.11 | 0.89 | 1.10 | −1.0% | 0.8032 |
| 7 | 1.15 | 0.92 | 1.14 | −1.2% | 0.8297 |
| 8 | 1.13 | 0.91 | 1.12 | −0.5% | 0.8432 |
| 9 | 1.11 | 0.89 | 1.10 | −1.0% | 0.8205 |
| 10 | 1.12 | 0.89 | 1.10 | −1.9% | 0.8147 |
| 11 | 1.1 | 0.89 | 1.10 | −0.1% | 0.8239 |
| 12 | 1.22 | 0.94 | 1.16 | −4.8% | 0.7962 |
| 13 | 1.17 | 0.91 | 1.12 | −3.9% | 0.8021 |

The average value for $a_1$ from Table 1 was 0.8097 (approximately 0.81), with a standard deviation of 0.03 and a CV of 3.3%.

Example 3

ISI Assignment for PT Test Strips Using Control Compositions with Plasma Standard Calibrants This example repeats the determination of the relationship between the PT test strips and reference thromboplastin using commercial calibration plasmas instead of plasma from 20 normal and 60 anticoagulant treated donors. Seven levels of Precision Biologics INR Calibration Plasma (Control Normal and Control Abnormal I through Control Abnormal VI) were used, and sample control compositions were prepared by mixing the plasma samples with combined particle suspension and pigmented calcium chloride solution in the manner described above. The logarithmic values of the PTs obtained from the RECOMBIPLASTIN® were plotted against the logarithmic values of the PTs obtained from the control composition samples made from the Precision Biologics Calibration Plasmas to provide a calibration line with slope $ISI_C$. The logarithmic values of the PTs obtained from the RECOMBIPLASTIN® using 80 donors' plasma were also plotted against the logarithmic values of the PTs obtained from the same capillary blood samples (20 normal, 80 abnormal) to provide a line with slope $ISI_{WB}$. The logarithmic values of the PTs obtained from the control composition samples were also plotted against the logarithmic values of the PTs obtained from the capillary blood samples to provide a line with slope a1. This procedure was repeated for each of nine three-channel test strips from ten different batches or lots of strips as prepared in Example 2 above. The $ISI_{WB}$, $ISI_C$, $ISI_C/a1$, and percent difference between $ISI_{WB}$ and $ISI_C/a1$ for each lot of test strips are shown in Table 2. The control compositions made from the commercial calibration plasmas provide good approximation of the corresponding calibration plasma standards for evaluation of the test strips.

TABLE 2

| Strip No. | $ISI_{WB}$ | $ISI_C$ | $ISI_C/0.8097$ | ISI % Difference |
|---|---|---|---|---|
| 1 | 1.09 | 0.89 | 1.10 | 0.8% |
| 2 | 1.11 | 0.9 | 1.11 | 0.1% |
| 3 | 1.11 | 0.88 | 1.09 | −2.1% |
| 4 | 1.11 | 0.92 | 1.14 | 2.4% |
| 5 | 1.12 | 0.91 | 1.12 | 0.3% |
| 6 | 1.1 | 0.91 | 1.12 | 2.2% |
| 7 | 1.22 | 0.98 | 1.21 | −0.8% |

TABLE 2-continued

| Strip No. | $ISI_{WB}$ | $ISI_C$ | $ISI_C/0.8097$ | ISI % Difference |
|---|---|---|---|---|
| 8 | 1.17 | 0.92 | 1.14 | -2.9% |
| 9 | 1.25 | 0.93 | 1.15 | — |

Example 4

Calibration Code Assignment for PT Test Strips

The geometric mean of the PTs of whole blood determined with the three-channel test strips of Example 2 was used as a whole blood MNPT value. Using the $ISI_C$ values obtained in Examples 3 and 4, calibration codes were calculated for the test strip lots. The calibration codes determined from WHO whole blood (Cal Code$_{WB}$) and from the control composition (Cal Code$_C$) are shown in Tables 3 and 4 respectively.

TABLE 3

| Strip No. | Cal Code$_{WB}$ | Cal Code$_C$ |
|---|---|---|
| 1 | 27 | 27 |
| 2 | 24 | 24 |
| 3 | 30 | 29 |
| 4 | 33 | 33 |
| 5 | 40 | 40 |
| 6 | 29 | 29 |
| 7 | 50 | 50 |
| 8 | 40 | 40 |
| 9 | 41 | 41 |
| 10 | 41 | 41 |
| 11 | 41 | 41 |
| 12 | 34 | 32 |
| 13 | 17 | 19 |

TABLE 4

| Strip No. | Cal Code$_{WB}$ | Cal Code$_C$ |
|---|---|---|
| 1 | 30 | 29 |
| 29 | 40 | 40 |
| 3 | 29 | 30 |
| 4 | 41 | 42 |
| 5 | 41 | 41 |
| 6 | 41 | 41 |
| 7 | 34 | 34 |
| 8 | 17 | 18 |
| 9 | <16 | 18 |

The average bias between ISI values estimated by the control compositions, either using the 20/60 citrated plasma samples of Example 2 and the Precision Biologics calibration plasmas of Example 3, and the WHO whole blood calibration, is less than 8%. Throughout the various lots of test strips and clinical offsite samples, the relationship between the control compositions and their corresponding blood counter $a_1$ remained relatively constant. The calibration code generated by the control compositions using either the 20/60 citrated plasma samples or the Precision Biologics calibrants are within ±2 calibration code range. Thus, the control compositions of the invention provide an effective way to assign ISI and calibration codes to PT test strips.

Example 5

Use of Control Composition for Test Strip Quality Control

Standard evaluation of in-vitro diagnostic devices requires a precision-testing component for defined end users. In this Example the total precision performance for the three-channel test strips of Example 1 was determined according to the procedures of NCCLS (National Committee for Clinical Lab Standards) Document EP5-A Vol. 19, No. 2 ("Evaluation of Precision Performance of Clinical Chemistry Devices; Approved Guideline"), the disclosure of which is incorporated herein by reference. NCCLS recommends a minimum of 20 operating days for precision evaluation experiments. Two separate lots of test strips were evaluated for performance at two independent investigation sites: the University of California at San Francisco, Department of Hematology/Oncology and Antigcoagulation clinic (UCSF); and the Oregon Health Sciences University Anticoagulation Clinic (OHSU) in Portland, Oreg.

Two levels of citrated plasma were obtained from Precision Biologics to perform testing. A level "1" control, with an approximate INR of 1.0, and a level "2" control with an INR of approximately 2.8 were used to assess precision. The plasma samples were stored frozen. Prior to use, an aliquot of each control plasma was thawed according to protocol, and each aliquot was combined with particle suspension and calcium chloride solution in the manner described in Example 1 prior to application to test strips. Three channel test strips as described in Example 2 above were used in this Example.

Twenty test strips were evaluated on the same day at each investigation site to provide a "within run" precision test. The "within run" precision test results are shown in Table 5.

TABLE 5

| UCSF Within Run Precision | | | OHSU Within Run Precision | | |
|---|---|---|---|---|---|
| Strip No. | $ISI_C/0.8097$ Level 1 | $ISI_C/0.8097$ Level 2 | Strip No. | $ISI_C/0.8097$ Level 1 | $ISI_C/0.8097$ Level 2 |
| 1 | 1.0 | 2.8 | 1 | 1.0 | 2.9 |
| 2 | 1.0 | 2.8 | 2 | 1.0 | 2.9 |
| 3 | 1.1 | 2.7 | 3 | 1.0 | 2.0 |
| 4 | 1.0 | 2.8 | 4 | 1.1 | 2.9 |
| 5 | 1.0 | 2.8 | 5 | 1.0 | 2.7 |
| 6 | 1.0 | 2.8 | 6 | 1.0 | 2.8 |
| 7 | 0.9 | 2.6 | 7 | 1.0 | 2.8 |
| 8 | 0.9 | 2.6 | 8 | 1.0 | 2.8 |
| 9 | 1.1 | 2.7 | 9 | 1.0 | 3.0 |
| 10 | 1.1 | 2.7 | 10 | 1.1 | 3.0 |
| 11 | 1.1 | 2.8 | 11 | 1.1 | 2.9 |
| 12 | 1.1 | 2.7 | 12 | 1.1 | 3.0 |
| 13 | 1.1 | 2.7 | 13 | 1.2 | 2.7 |
| 14 | 1.0 | 2.7 | 14 | 1.1 | 2.9 |
| 15 | 1.1 | 2.7 | 15 | 1.1 | 3.2 |
| 16 | 1.0 | 2.8 | 16 | 1.1 | 3.1 |
| 17 | 1.1 | 2.9 | 17 | 1.0 | 2.9 |
| 18 | 1.1 | 3.0 | 18 | 1.2 | 2.7 |
| 19 | 1.0 | 2.7 | 19 | 1.1 | 3.2 |
| 20 | 1.0 | 2.6 | 20 | 1.2 | 3.2 |
| Mean | 1.0 | 2.7 | Mean | 1.1 | 2.9 |
| SD | 0.04 | 0.07 | SD | 0.05 | 0.14 |
| % CV | 3.8 | 2.8 | % CV | 5.0 | 4.7 |

The "between day" precision was also determined at the two investigation sites using 80 test strips per control level over a 20 day period at each investigation site. The results of the between day precision evaluation are shown in Table 6.

TABLE 6

| | UCSF Between Day Precision | | OHSU Between Day Precision | |
|---|---|---|---|---|
| | Level 1 | Level 2 | Level 1 | Level 2 |
| Mean | 1.0 | 2.7 | 1.1 | 3.0 |
| SD | 0.092 | 0.201 | 0.083 | 0.226 |
| % CV | 9.1 | 7.4 | 7.2 | 7.7 |

As can be seen from Table 5 and Table 6, the %CV (coefficient of variation) using the control composition for the within run precision test was 5% or less at each investigation site. The %CV for the between day precision test for the control composition was less than 10% at each investigation site.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A control composition for a coagulation test, comprising:
    (a) plasma aggregatable particles; and
    (b calcium ions and;
    (c) hemoglobin.
2. The control composition of claim 1, further comprising at least one optical contrast enhancer.
3. The control composition of claim 1, wherein said particles comprise polymeric beads having charged functional groups on surfaces thereof.
4. The control composition of claim 1, wherein said calcium ions comprise a calcium halide.
5. The control composition of claim 1, further comprising plasma.
6. A control composition for a coagulation test, comprising:
    (a) plasma aggregatable particles;
    (b) a solution of calcium ions;
    (c) plasma; and
    (d) hemoglobin.
7. The control composition of claim 6, wherein said solution of calcium ions further comprises an optical contrast enhancer.
8. The control composition of claim 6, wherein said solution of calcium ions further comprises a dissolved dye.
9. The control composition of claim 6, wherein said particles are suspended in a solution comprising an antifreeze.
10. The control composition of claim 6, wherein said particles comprise polymeric beads having charged functional groups on surfaces thereof.
11. The control composition of claim 10, wherein said polymeric beads comprise polystyrene, and said charged functional groups comprise carboxylate groups.
12. The control composition of claim 10, wherein said polymeric beads contain a dye.
13. A control composition for a coagulation test, comprising:
    (a) a suspension of polymeric beads having charged functional groups on surfaces of said beads;
    (b) a solution of calcium ions;
    (c) citrated plasma; and
    (d) hemoglobin.
14. The control composition of claim 13, wherein said solution of calcium ions includes an optical contrast enhancer.
15. The control composition of claim 13, wherein said solution of calcium ions comprises a calcium halide solution.
16. The control composition of claim 13, wherein said polymeric beads comprise polystyrene.
17. The control composition of claim 13, wherein said charged functional groups comprise carboxylato groups.
18. The control composition of claim 13, wherein said polymeric beads contain a dye.
19. The control composition of claim 13, wherein said suspension of polymeric beads further comprises an antifreeze.
20. The control composition of claim 13, wherein said solution of calcium ion further comprises a dissolved dye.
21. A method for evaluating a coagulation test, comprising:
    (a) providing a composition including calcium ions hemoglobin and plasma aggregatable particles;
    (b) combining said calcium ions hemoglobin and said particles with plasma to form a control composition; and
    (c) introducing said control composition and to said coagulation test.
22. The method of 21, further comprising monitoring coagulation of said control composition.
23. The method of claim 22, further comprising determining a coagulation time for said control composition.
24. The method of claim 23, further comprising determining a relationship between said coagulation time of said control composition and a coagulation time of whole blood associated with said plasma in said control composition.
25. The method of claim 24, further comprising determining a relationship between said coagulation time for said control composition, and a coagulation time using a reference test.
26. The method of claim 25, further comprising determining a calibration curve for said coagulation test.
27. The method of claim 21, wherein said coagulation test comprises a prothrombin time test.
28. The method of claim 21, wherein said providing said composition comprises:
    (a) providing a suspension of said particles;
    (b) providing a solution of said calcium ions; and
    (c) providing a hemoglobin solution and
    (d) combining said suspension of said particles, said hemoglobin solution and said solution of calcium ions.
29. The method of claim 28, wherein said particles comprise polymeric beads having charged functional groups on surfaces thereof.
30. The method of claim 21, wherein providing said composition comprises including at least one optical contrast enhancer in said composition.

31. A method for evaluating a coagulation test, comprising:
   (a) providing plasma aggregatable particles;
   (b) providing a solution of calcium ions and a solution containing hemoglobin;
   (c) combining said particles with said solution of said calcium ions and said solution containing hemoglobin;
   (d) adding citrated plasma to said combined said particles and said solutions of said calcium ions and hemoglobin to form a control composition; and
   (e) introducing said control composition to a coagulation test.

32. The method of claim 31, further comprising monitoring coagulation of said control composition.

33. The method of claim 32, further comprising determining a coagulation time for said control composition.

34. The method of claim 33, further comprising determining a relationship between said coagulation time of said control composition, and a coagulation time of whole blood associated with said plasma in said control composition.

35. The method of claim 34, further comprising determining a relationship between said coagulation time for said control composition and a coagulation time using a reference test.

36. The method of claim 35, further comprising determining a calibration curve for said coagulation test.

37. The method of claim 31, wherein said solution of said calcium ions comprises an aggregation enhancer.

38. The method of claim 37, wherein said aggregation enhancer comprises hemoglobin.

39. The method of claim 31, wherein said particles comprise polymeric beads with charged functional groups on surfaces thereof.

40. The method of claim 31, wherein said solution of said calcium ions comprises a calcium halide solution.

41. The method of claim 31, wherein said providing said particles comprises suspending said particles in an antifreeze.

42. The method of claim 31, wherein said coagulation test comprises a prothrombin time test.

* * * * *

UNITED STATES PATENT AND TRADEMARK OFFICE
CERTIFICATE OF CORRECTION

PATENT NO. : 6,746,872 B2
DATED : June 8, 2004
INVENTOR(S) : Xiang Yang Zheng et al.

It is certified that error appears in the above-identified patent and that said Letters Patent is hereby corrected as shown below:

Column 21,
Line 33, the word "and" after the ";" should be removed.
Line 34, a -- ; -- should be inserted after the word "ions" and before the word "and".
Line 34, the ";" after the word "and" should be removed.

Column 22,
Line 19, the word "carboxylato" should be replaced with the word -- carboxylate --.
Lines 29 and 31, a -- , -- should be inserted after the word "ions" and before the word "hemoglobin".
Line 57, the word "and" should be removed after the ";".
Line 58, a -- ; -- should be inserted after the word "solution" and before the word "and".
Line 61, the word -- said -- should be inserted after the word "of" and before the word "calcium".

Column 24,
Line 3, a -- , -- should be inserted after the word "composition" and before the word "and".

Signed and Sealed this

Twenty-first Day of December, 2004

JON W. DUDAS
*Director of the United States Patent and Trademark Office*